United States Patent
Kang et al.

(10) Patent No.: US 10,578,765 B2
(45) Date of Patent: Mar. 3, 2020

(54) SCAN METHOD, SCAN SYSTEM AND RADIATION SCAN CONTROLLER

(71) Applicants: NUCTECH COMPANY LIMITED, Beijing (CN); TSINGHUA UNIVERSITY, Beijing (CN)

(72) Inventors: Kejun Kang, Beijing (CN); Yaohong Liu, Beijing (CN); Ziran Zhao, Beijing (CN); Wei Jia, Beijing (CN); Jianping Gu, Beijing (CN); Chuanxiang Tang, Beijing (CN); Huaibi Chen, Beijing (CN); Jianjun Gao, Beijing (CN); Wei Yin, Beijing (CN); Xiying Liu, Beijing (CN)

(*) Notice: Subject to any disclaimer, the term of this patent is extended or adjusted under 35 U.S.C. 154(b) by 0 days.

(21) Appl. No.: 16/253,221

(22) Filed: Jan. 22, 2019

(65) Prior Publication Data
US 2019/0170894 A1    Jun. 6, 2019

Related U.S. Application Data (63) Continuation of application No. 15/289,206, filed on Oct. 10, 2016.

(30) Foreign Application Priority Data

Dec. 23, 2015    (CN) .......................... 2015 1 0976300

(51) Int. Cl.
*G01V 5/00* (2006.01)
*G01T 1/29* (2006.01)
*G01N 23/04* (2018.01)

(52) U.S. Cl.
CPC ........... *G01V 5/0016* (2013.01); *G01N 23/04* (2013.01); *G01T 1/29* (2013.01)

(58) Field of Classification Search
None
See application file for complete search history.

(56) References Cited

U.S. PATENT DOCUMENTS 8,541,756 B1    9/2013  Treas
9,086,496 B2    7/2015  Star-Lack et al.
(Continued)

FOREIGN PATENT DOCUMENTS

RU    2430424 C1     9/2011
WO    2011115927 A2  9/2011

OTHER PUBLICATIONS

Russian Office Action dated Mar. 20, 2019 in the corresponding Russian application (application No. 2016140416).
(Continued)

*Primary Examiner* — Hoon K Song
(74) *Attorney, Agent, or Firm* — Kilpatrick Townsend & Stockton, LLP (57) ABSTRACT

This invention provides a scan method, scan system and radiation scan controller, and relates to the field of radiation. The scanning method includes obtaining detection data of an object to be inspected under radiation scanning using a detector, adjusting an accelerator output beam dose rate and/or an output electron beam energy level of a radiation emission device according to the detection data. With this method, working conditions of the accelerator of the radiation emission device may be adjusted according to the detection data detected by the detector, so that for a region having a larger mass thickness, a higher output beam dose rate or a higher electron beam output energy level is adopted to guarantee satisfied imaging technical indexes, for a region having a smaller mass thickness, a lower output beam dose rate or a lower electron beam output energy level is adopted (Continued)

to reduce the environmental dose level while guaranteeing satisfied imaging technical indexes.

13 Claims, 6 Drawing Sheets

(56) References Cited

U.S. PATENT DOCUMENTS

| | | | | |
|---|---|---|---|---|
| 2006/0104414 A1* | 5/2006 | Mayo | ................... | G01N 23/20 |
| | | | | 378/57 |
| 2011/0038453 A1* | 2/2011 | Morton | ............... | G01V 5/0016 |
| | | | | 378/57 |
| 2012/0294422 A1* | 11/2012 | Cheung | ................... | H05H 7/02 |
| | | | | 378/65 |

OTHER PUBLICATIONS

Russian Search Report completed on Mar. 19, 2019 in the corresponding Russian application (application No. 2016140416).

* cited by examiner

SCAN METHOD, SCAN SYSTEM AND RADIATION SCAN CONTROLLER

CROSS-REFERENCES TO RELATED APPLICATIONS

The present application claims the priority of Chinese Application No. 201510976300.8, filed in the Chinese Patent Office on Dec. 23, 2015 and is a continuation application of U.S. application Ser. No. 15/289,206, filed on Oct. 10, 2016, both of the entire contents are herein incorporated by reference.

FIELD

This invention relates to the field of radiation, particularly to a scan method, scan system and controller.

BACKGROUND

Currently, most of the X-ray light sources used in real-time containers/vehicle scanning and imaging systems are produced by linear electron accelerators having constant output dose rates. In general, imaging technical indexes of an inspection system, especially system penetrability, depends on the output dose rate of its accelerator, i.e., the higher the dose rate is, the better the penetrability is. However, since X-ray may cause radiation damage to human bodies and the environment, it is necessary to control the accelerator output dose rate in operation, or provide additional shielding protection or other measures, to meet the requirement of the environmental dose level.

In order to meet the requirements for scanning under various different conditions, the accelerators' dose rates and energy levels of imaging systems are usually set to their maximum penetration and material resolution setting values that are allowed by the systems. However, in actual situation, the cargoes under inspection or the amounts of cargoes carried by containers/vehicles are usually different, so, the requirements of X-ray output dose rates and energy levels for a particular scan imaging system may vary greatly, which may cause a dose rate above an actually required value in scanning, additional shielding protection cost, or unnecessary radiation to relevant operators. If a suitable accelerator dose rate or electron beam energy level may be selected according to actual situations of cargoes to be inspected, an imaging inspection system that may guarantee satisfied system imaging technical indexes and image quality without causing unnecessary cost for radiation shielding protection may be realized, which has important practical significance.

There is a technique in the prior art for imaging different regions of an object to be inspected using a multi-dose and multi-energy accelerator, which mainly relates to a fast inspection system, for example, a head region of a vehicle where the driver locates may be scanned at a lower safety dose rate which may not cause damage to the driver, and a cargo region of the vehicle may be scanned at a higher dose rate. This scheme has gained successful applications in X-ray fast inspection system devices, however, it cannot be adjusted according to varied situations of cargoes, and thus has certain limitation.

SUMMARY

An object of this invention is to provide a solution capable of taking both the requirement of imaging technical indexes of as system and the requirement of the environmental dose level into consideration.

According to an aspect of this invention, a scan method is provided, comprising: acquiring detection data of an object to be inspected under radiation scanning using a detector; adjusting an accelerator output beam dose rate and/or an output electron beam energy level of a radiation emission device according to the detection data.

Optionally, the detection data comprises a sampling value of the detector and/or transparency information of the object to be inspected; adjusting an accelerator output beam dose rate and/or an output electron beam energy level of a radiation emission device according to the detection data comprises: adjusting an accelerator output beam dose rate and/or an output electron beam energy level of a radiation emission device according to the sampling value and/or transparency information of the object to be inspected.

Optionally, adjusting an accelerator output beam dose rate and/or an output electron beam energy level of a radiation emission device according to the detection data comprises: during a movement of the object to be inspected relative to the radiation emission device and the detector, adjusting an accelerator output beam dose rate and/or an output electron beam energy level of a radiation emission device according to real-time detection data obtained by the detector from a scanning region of the object to be inspected.

Optionally, adjusting an accelerator output beam dose rate and/or an output electron beam energy level of a radiation emission device according to the detection data comprises: acquiring overall scanning data of the object to be inspected using the detector; analyzing the overall scanning data to determine a main scanning region of the object to be inspected, wherein the main scanning region comprises a low penetration region or a region suspected to be a contraband item; determine an accelerator output beam dose rate and/or an output electron beam energy level according to detection data of the main scanning region, to scan the main scanning region.

Optionally, the detection data is a sampling value of a detection region; adjusting an output electron beam energy level of a radiation emission device according to the detection data comprises: comparing the sampling value with a predetermined sampling threshold value; if the sampling value is below a predetermined lower sampling threshold value, increasing the accelerator output beam dose rate and/or the output electron beam energy level; if the sampling value is above a predetermined upper sampling threshold value, decreasing the accelerator output beam dose rate and/or the output electron beam energy level.

Optionally, acquiring detection data of an object to be inspected under radiation scanning through a detector comprises: dividing data acquired by the detector into sections according to a predetermined detection granularity; using an average value of data items from the same section as the sampling value; or extracting a minimum value of data items from the same section as the sampling value.

Optionally, the detection data is transparency information of the object to be inspected; adjusting an accelerator output beam dose rate and/or an output electron beam energy level of a radiation emission device according to the detection data comprises: comparing the transparency information with a predetermined transparency threshold value; if the transparency information is below a predetermined lower transparency threshold value, increasing the accelerator output beam dose rate and/or the output electron beam energy level; if the transparency information is above a predetermined upper transparency threshold value, decreasing the accelerator output beam dose rate and/or the output electron beam energy level.

Optionally, acquiring detection data of an object to be inspected under radiation scanning through a detector comprises: acquiring initial transparency information according to the detection data; correcting the initial transparency information according to a background image and an air image to obtain the transparency information.

Optionally, adjusting an accelerator output beam dose rate and/or an output electron beam energy level of a radiation emission device according to the detection data comprises: determining an ideal output beam dose rate and/or an ideal output electron beam energy level according to a conversion policy for converting the detection data to the ideal accelerator output beam dose rate and/or the ideal output electron beam energy level; adjusting the accelerator output beam dose rate and/or the output electron beam energy level to the ideal output beam dose rate and/or the ideal output electron beam energy level.

Optionally, the accelerator of the radiation emission device comprises multiple output beam dose rate levels and/or multiple output electron beam energy levels, each level having a fixed output beam dose rate and/or a fixed output electron beam energy value; adjusting an accelerator output beam dose rate and/or an output electron beam energy level of a radiation emission device according to the detection data comprises: adjusting the accelerator output beam dose rate and/or the output electron beam energy level of the radiation emission device to a certain level according to the detection data.

With this method, working conditions of the accelerator of the radiation emission device may be adjusted according to the detection data detected by the detector, so that for a region having a larger mass thickness, a higher output beam dose rate or a higher electron beam output energy level is adopted to guarantee satisfied imaging technical indexes, for a region having a smaller mass thickness, a lower output beam dose rate or a lower electron beam output energy level is adopted to reduce the environmental dose level while guaranteeing satisfied imaging technical indexes.

According to another aspect of this invention, a radiation scan controller is provided, comprising: a data acquisition module for acquiring detection data of an object to be inspected under radiation scanning using a detector; an adjustment module for adjusting an accelerator output beam dose rate and/or an output electron beam energy level of a radiation emission device according to the detection data.

Optionally, the detection data comprises a sampling value of the detector and/or transparency information of the object to be inspected; the adjustment module is further used to adjust an accelerator output beam dose rate and/or an output electron beam energy level of a radiation emission device according to the sampling value and/or transparency information of the object to be inspected.

Optionally, the adjustment module is further used to: during a movement of the object to be inspected relative to the radiation emission device and the detector, adjust the accelerator output beam dose rate and/or the output electron beam energy level of the radiation emission device according to real-time detection data obtained by the detector from a scanning region of the object to be inspected.

Optionally, the adjustment module is further used to: acquire overall scanning data of the object to be inspected; analyze the overall scanning data to determine a main scanning region of the object to be inspected, wherein the main scanning region comprises a low penetration region or a region suspected to be a contraband item; determine an accelerator output beam dose rate and/or an output electron beam energy level according to detection data of the main scanning region, to scan the main scanning region.

Optionally, the detection data is a sampling value of a detection region; the adjustment module comprises: a comparison unit for comparing the sampling value with a predetermined sampling threshold value; an emission adjustment unit for, if the sampling value is below a predetermined lower sampling threshold value, increasing the accelerator output beam dose rate and/or the output electron beam energy level; if the sampling value is above a predetermined upper sampling threshold value, decreasing the accelerator output beam dose rate and/or the output electron beam energy level.

Optionally, the data acquisition module is further used to: divide data acquired by the detector into sections according to a predetermined detection granularity; use an average value of data items from the same section as the sampling value; or extract a minimum value of data items from the same section as the sampling value.

Optionally, the detection data is transparency information of the object to be inspected; the adjustment module further comprises: a comparison unit for comparing the transparency information with a predetermined transparency threshold value; an emission adjustment unit for, if the transparency information is below a predetermined lower transparency threshold value, increasing the accelerator output beam dose rate and/or the output electron beam energy level; if the transparency information is above a predetermined upper transparency threshold value, decreasing the accelerator output beam dose rate and/or the output electron beam energy level.

Optionally, the data acquisition module is further used to: acquire initial transparency information according to the detection data; correct the initial transparency information according to a background image and an air image to obtain the transparency information.

Optionally, the adjustment module further comprises: an ideal value determination unit for determining an ideal output beam dose rate and/or an ideal output electron beam energy level according to a conversion policy for converting the detection data to the ideal accelerator output beam dose rate and/or the ideal output electron beam energy level; an emission adjustment unit for adjusting the accelerator output beam dose rate and/or the output electron beam energy level to the ideal output beam dose rate and/or the ideal output electron beam energy level.

Optionally, the accelerator of the radiation emission device comprises multiple output beam dose rate levels and/or multiple output electron beam energy levels, each level having a fixed output beam dose rate and/or a fixed output electron beam energy value; the adjustment module is further used to adjust the accelerator output beam dose rate and/or the output electron beam energy level of the radiation emission device to a certain level according to the detection data.

This controller may adjust working conditions of the accelerator of the radiation emission device according to the detection data detected by the detector, so that for a region having a larger mass thickness, a higher output beam dose rate or a higher electron beam output energy level is adopted to guarantee satisfied imaging technical indexes, for a region having a smaller mass thickness, a lower output beam dose rate or a lower electron beam output energy level is adopted to reduce the environmental dose level while guaranteeing satisfied imaging technical indexes.

According to still another aspect of this invention, a scan system is provided, comprising: any controller, detector and radiation emitter mentioned above; wherein the detector is used to send detection data to the controller; the controller is used to send control information to the radiation emitter for adjusting an accelerator output beam dose rate and/or an output electron beam energy level of the radiation emission device according to the detection data; the radiation emitter is used to emit radiation, adjust the accelerator output beam dose rate and/or the output electron beam energy level of the radiation emission device according to the control information.

This scan system may adjust working conditions of the accelerator of the radiation emission device according to the detection data detected by the detector, so that for a region having a larger mass thickness, a higher output beam dose rate or a higher electron beam output energy level is adopted to guarantee satisfied imaging technical indexes, for a region having a smaller mass thickness, a lower output beam dose rate or a lower electron beam output energy level is adopted to reduce the environmental dose level while guaranteeing satisfied imaging technical indexes.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention, but are not limitation thereof. In the drawings.

DETAILED DESCRIPTION OF THE INVENTION

Below, the technical solution of this invention will be further described in detail with reference to the accompanying drawings and embodiments.

Figure 1:
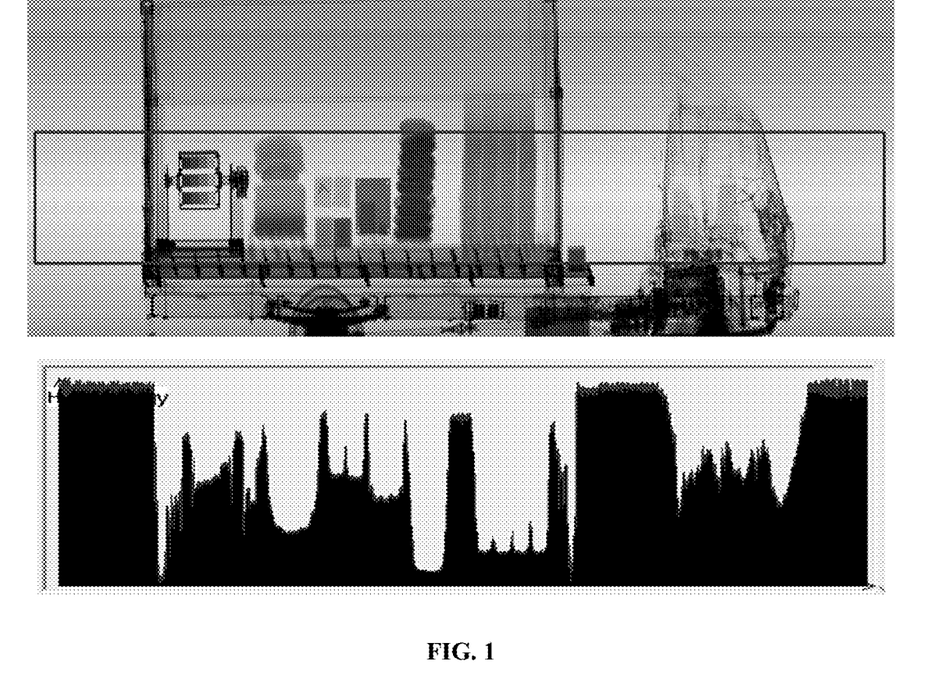
FIG. 1 is a schematic view showing the principle of the scan method of this invention.

In a process of radiation detection, different data may be obtained by a detector from different regions of an object to be inspected due to its interior inhomogeneity. As shown in FIG. 1, an object to be inspected which is a vehicle is shown in the upper portion of FIG. 1, and detection data of corresponding locations is shown in the lower portion. It can be seen from FIG. 1, low energy radiation is obtained by the detector from locations on the vehicle having large mass thicknesses; from locations on the vehicle having smaller mass thicknesses or empty regions, high energy radiation is obtained by the detector. Based on the above reasons, a higher accelerator output beam dose rate or a higher electron output beam energy level may be adopted for locations having larger mass thicknesses, and a lower accelerator output beam dose rate or a lower electron output beam energy level may be adopted for locations having smaller mass thicknesses.

Figure 2:
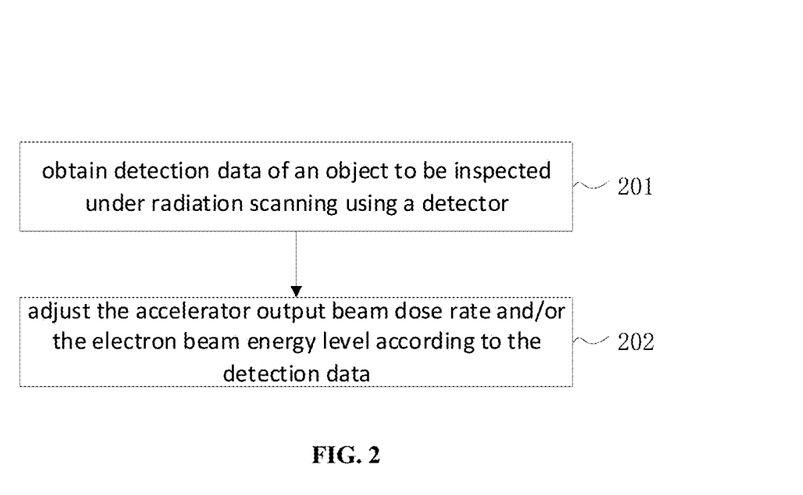
FIG. 2 is a flow chart of an embodiment of the scan method of this invention.

FIG. 2 is a flow chart of an embodiment of the scan method of this invention.

At step 201, detection data of an object to be inspected under radiation scanning is obtained using a detector.

At step 202, working conditions of a radiation emitter are adjusted according to the detection data acquired by the detector. Working conditions of the radiation emitter comprise an accelerator output beam dose rate and an electron beam energy level. The accelerator output beam dose rate, or the output electron beam energy level, or both of them may be adjusted.

With this method, working conditions of the accelerator of the radiation emission device may be adjusted according to the detection data detected by the detector, so that for a region having a larger mass thickness, a higher output beam dose rate or a higher electron beam output energy level is adopted to guarantee satisfied imaging technical indexes, for a region having a smaller mass thickness, a lower output beam dose rate or a lower electron beam output energy level is adopted to reduce the environmental dose level while guaranteeing satisfied imaging technical indexes.

In an embodiment, the detection data may be a sampling value of the detector, working conditions of the radiation emitter are adjusted according to the sampling value; or the detection data may be transparency information of the object to be inspected obtained by the detector, and working conditions of the radiation emitter are adjusted according to the transparency information. In this manner, working conditions of a radiation emitter may be determined according to a sampling value obtained by the detector or transparency information of a detection image. This may facilitate data acquiring and processing, so that the response speed of the system may be increased.

In an embodiment, if the radiation emitter is a dual-energy device, real-time material discrimination may be performed based on the detection data to obtain atomic numbers and mass thickness values, and working conditions of the radiation emitter may be adjusted based on these informations.

Figure 3:
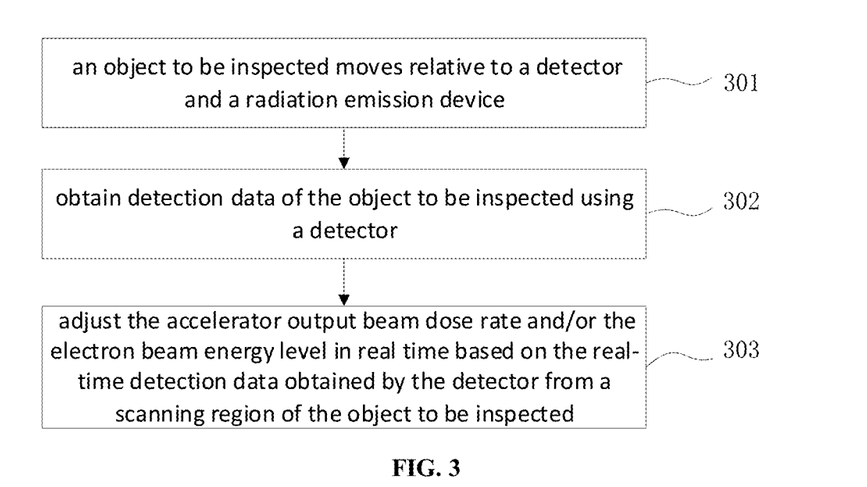
FIG. 3 is a flow chart of another embodiment of the scan method of this invention.

FIG. 3 is a flow chart of another embodiment of the scan method of this invention.

At step 301, an object to be inspected moves relative to a detector and a radiation emission device. The object to be inspected gradually passes through an electron beam projection region of the radiation emission device.

At step 302, the detector obtains real-time detection data from a scanned region of the object to be inspected.

At step 303, working conditions of the radiation emission device's accelerator are adjusted based on the real-time detection data. In an embodiment, the real-time detection data is a sampling value, at the beginning of a scanning process (generally, in the event of air or empty space), the accelerator has a lower dose rate or a lower output beam energy level. When the detector detects that the sampling value becomes larger, it indicates that the object to be inspected entering the detection range has a smaller mass thickness, thus the output beam dose rate or the electron beam output energy level may be decreased. When the sampling value becomes smaller, it indicates that the object to be inspected entering the detection range has a larger mass thickness, thus the output beam dose rate or the electron beam output energy level may be increased. In another embodiment, transparency information of the object to be inspected is used as real-time detection data, when the detector detects an increase in the transparency information, it indicates that the object to be inspected entering the detection range has a smaller mass thickness, thus the output beam dose rate or the electron beam output energy level may be decreased. When a decrease in the transparency information is detected, it indicates that the object to be inspected entering the detection range has a larger mass thickness, thus the output beam dose rate or the electron beam output energy level may be increased.

In this manner, the accelerator's output beam dose rate and/or electron beam output energy level may be adjusted in real time during the scanning process, so that detection may be completed in one operation while guaranteeing satisfied imaging technical indexes and reducing environmental dose level to improve detection efficiency.

Figure 4:
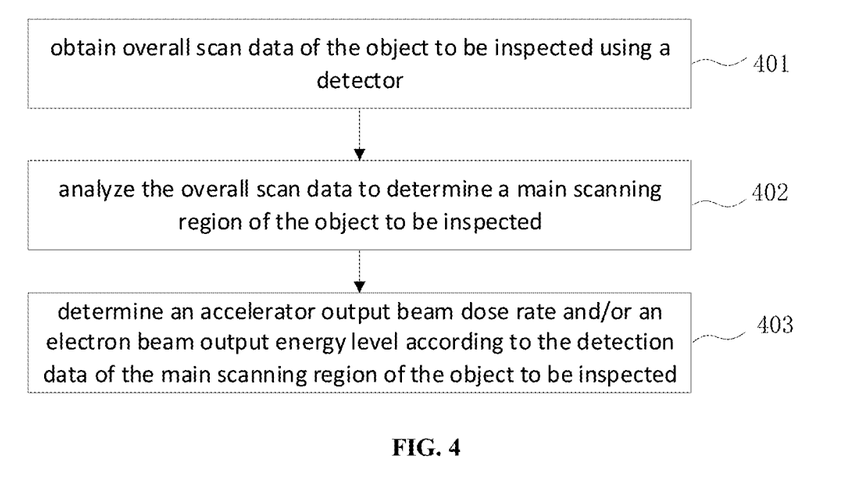
FIG. 4 is a flow chart of another embodiment of the scan method of this invention.

FIG. 4 is a flow chart of another embodiment of the scan method of this invention.

At step 401, detection is performed with a predetermined standard accelerator output beam dose rate and an electron beam output energy level on an object to be inspected in its entirety. Overall scan data of the object to be inspected is obtained using a detector.

At step 402, the overall scan data is analyzed to determine a main scanning region of the object to be inspected. The main scanning region may be a low penetration region determined from the overall scan data or a region suspected to be a contraband item.

At step 403, the accelerator output beam dose rate/the electron beam output energy level is increased to detect the main scanning region again. The particular accelerator output beam dose rate/electron beam output energy level may be determined according to the obtained scan data.

In this manner, a main scanning region may be obtained from the scan data, and only the main scanning region is detected using a higher accelerator output beam dose rate and/or a higher electron beam output energy level to realize satisfied imaging technical indexes and a reduced environmental dose level. Compared with real-time detection and adjustment, this method has a lower requirement of system response speed and is more accurate, it also allows the object to be inspected to pass through the detection region at a faster speed.

Figure 5:
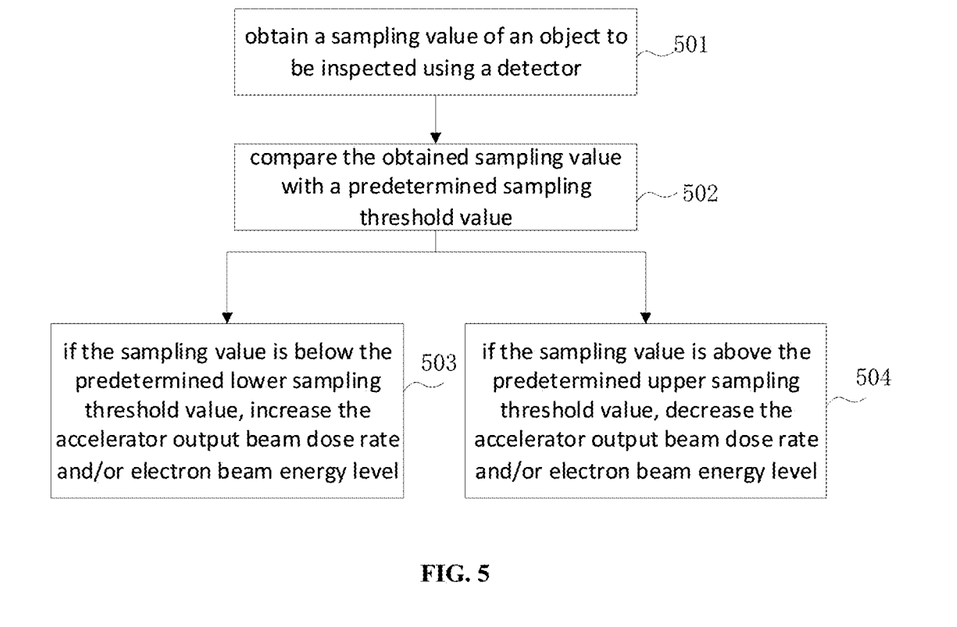
FIG. 5 is a flow chart of another embodiment of the scan method of this invention.

FIG. 5 is a flow chart of another embodiment of the scan method of this invention.

Figure 6:
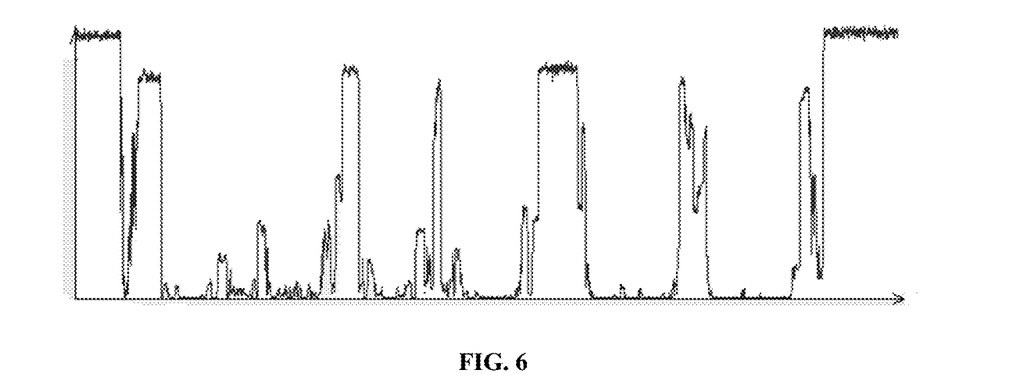
FIG. 6 is a schematic view of determining a sampling value in the scan method of this invention.

At step 501, a sampling value of an object to be inspected is obtained using a detector. In the case of detecting the object to be inspected with the same working conditions of the radiation emission device, information of sampling values obtained by the detector is shown in FIG. 6. The sampling values detected by the detector change with mass thicknesses of the object to be inspected at different locations.

At step 502, the obtained sampling value is compared with a predetermined sampling threshold value. The predetermined sampling threshold value may comprise a predetermined lower sampling threshold value and a predetermined upper sampling threshold value. If the sampling value is below the predetermined lower sampling threshold value, step 503 is executed; if the sampling value is above the predetermined upper sampling threshold value, step 504 is executed.

At step 503, because the sampling value is below the predetermined lower sampling threshold value, it is considered that a corresponding location of the object to be inspected has a larger mass thickness, and the accelerator output beam dose rate/electron beam energy level will be increased.

At step 504, because the sampling value is above the predetermined upper sampling threshold value, it is considered that a corresponding location of the object to be inspected has a smaller mass thickness, and the accelerator output beam dose rate/electron beam energy level will be decreased.

In this manner, the obtained sampling value may be compared with the predetermined threshold value to determine whether it is necessary to adjust the accelerator output beam dose rate/electron beam energy level and how to adjust the accelerator output beam dose rate/electron beam energy level, which has advantages of clear in logic, concise calculation, low requirements of the processing device, and easy to be popularized and applied. Meanwhile, adjustment is required only if a certain threshold value has been reached, so that the number of times the adjustment is performed may be reduced, and the device load may be decreased.

In an embodiment, several factors must be taken into consideration when determining the sampling value, including a current dose rate and angular distribution of the accelerator, the fluctuation in the dose rate and various inconsistency between accelerator sparking and the amplification factor of the detector, etc. In an embodiment, division may be performed according to a predetermined detection granularity, and an average value of several selected sampling values obtained by the detector nearby a main beam may be used as the sampling value, or a minimum value of single-point sampling values within a section may be used as the sampling value of this section. This approximate estimation method has a simple operation flow and does not need real-time image correction, so that the processing speed may be increased and system requirements may be reduced. In an embodiment, a minimum value may be determined through performing filtering on the collected data. This method takes influences on the system and environment into account and may improve accuracy.

Figure 7:
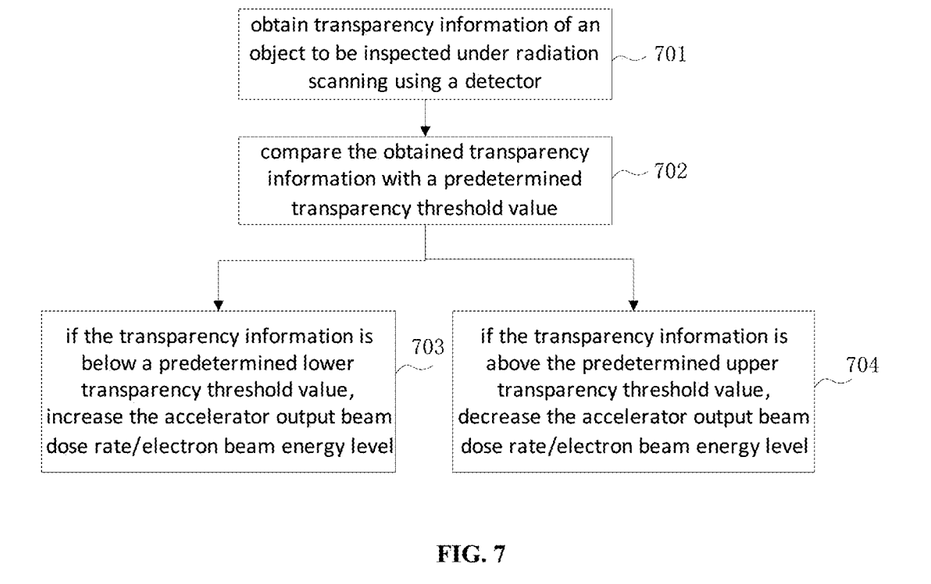
FIG. 7 is a flow chart of another embodiment of the scan method of this invention.

FIG. 7 is a flow chart of another embodiment of the scan method of this invention.

Figure 8:
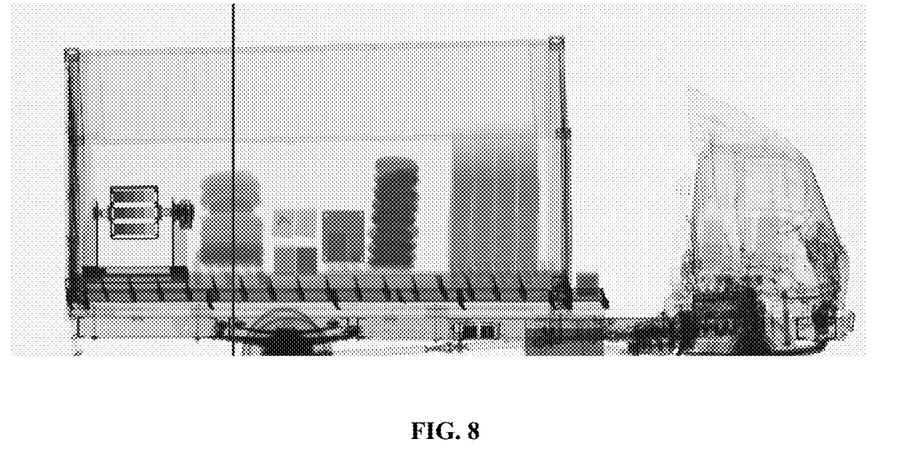
FIG. 8 is a schematic view of transparency determination in the scan method of this invention.

At step 701, transparency information of an object to be inspected under radiation scanning is obtained using a detector. If the radiation emission device radiates the object to be inspected under constant working conditions, transparency information of the object to be inspected in a detection image generated from the data obtained by the detector is shown in FIG. 8.

At step 702, the obtained transparency information is compared with a predetermined transparency threshold value. The predetermined transparency threshold value may comprise a predetermined lower transparency threshold value and a predetermined upper transparency threshold value. If the transparency information is below the predetermined lower transparency threshold value, step 703 is executed; if the transparency information is above the predetermined upper transparency threshold value, step 704 is executed;

At step 703, because the transparency information is below the predetermined lower transparency threshold value, it is considered that a corresponding location of the object to be inspected has a larger mass thickness, and the accelerator output beam dose rate/electron beam energy level will be increased.

At step 704, because the transparency information is above the predetermined upper transparency threshold value, it is considered that a corresponding location of the object to be inspected has a smaller mass thickness, and the accelerator output beam dose rate/electron beam energy level will be decreased.

In this manner, the obtained transparency information may be compared with the predetermined threshold value to determine whether it is necessary to adjust the accelerator output beam dose rate/electron beam energy level and how to adjust the accelerator output beam dose rate/electron beam energy level, which has advantages of clear in logic, concise calculation, low requirements of the processing device, and easy to be popularized and applied. Meanwhile, adjustment is required only if a certain threshold value has been reached, so that the number of times the adjustment is performed may be reduced, and the device load may be decreased.

In an embodiment, first, initial transparency information of a detection region (for example, a column or several columns) may be obtained, as shown by a vertical line in FIG. 8, then initial transparency information is corrected according to a local image and an air image, for example, through subtracting a local image value, dividing by an air image value or multiplying by a brightness correction coefficient, to obtain transparency information of the object to be inspected. Due to differences in circuit designs and fabrication processes, different background images may be generated from natural background radiation and circuit noise data; meanwhile, due to the impact of environment and brightness, different air images and brightness information may be produced. In an embodiment, a statistic on transparency information of a detection region (for example, a column or several columns) may be obtained and an average value may be used as the transparency information. In this manner, by means of transparency information of the object to be inspected which has been corrected based on the impact of their environment, device conditions and other factors, detection accuracy may be guaranteed.

In an embodiment, ideal accelerator working conditions may be determined based on the detection data and a predetermined policy. According to the obtained detection data, based on a predetermined conversion policy, such as a linear relationship or a conversion formula, an ideal accelerator output beam dose rate or an ideal electron beam output energy level may be determined, so that working conditions of the radiation emitter may be adjusted based on the ideal values. In this manner, working conditions of the radiation emitter may be adjusted with a smaller granularity and more accurately, so that detection accuracy may be further improved.

Figure 9:
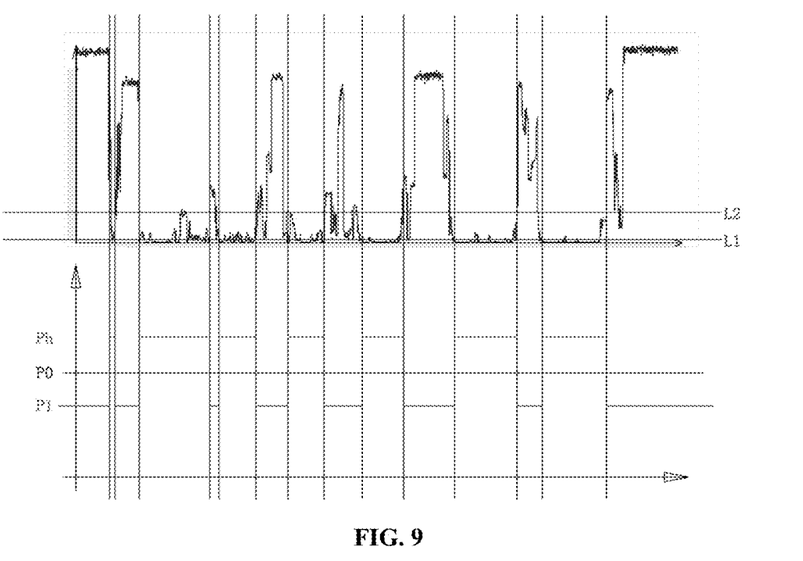
FIG. 9 is a schematic view of level determination in the scan method of this invention.

In an embodiment, the accelerator has three output beam dose rate levels, as shown in FIG. 9, including a high output beam dose rate Ph, a standard output beam dose rate P0 and a low output beam dose rate P1. In the case of detecting the object to be inspected with P0, if the detection data is above an upper threshold value Th, the output beam dose rate is adjusted to P1; if the detection data is below a lower threshold value T1, the output beam dose rate is adjusted to Ph. During a scanning, working conditions of the radiation emission device may be adjusted several times. In this manner, the accelerator output beam dose rate may be adjusted through a simple decision process, and only three conditions of the output beam dose rate are required for the accelerator to meet its demands, so that device requirements may be reduced, which is adverse to popularization and application.

In an embodiment, the accelerator has multiple output beam dose rate levels, such as P1, P2, . . . Pn(n>3) from low to high, when the object to be inspected is detected with Px, if the detection data is above an upper threshold value Th, the output beam dose rate is adjusted to Px−1; if the detection data is below a lower threshold value T1, the output beam dose rate is adjusted to Px+1. In this manner, through setting multiple levels, the output beam dose rate may be controlled more accurately and conveniently, and an optimal effect of controlling imaging technical indexes and reducing the environmental dose level may be achieved.

In an embodiment, three output electron beam energy levels are represented by Ph, P0 and P1 as shown in FIG. 9, when the object to be inspected is detected with P0, if the detection data is above an upper threshold value Th, the output electron beam energy level is adjusted to P1; if the detection data is below a lower threshold value T1, the output electron beam energy level is adjusted to Ph. In this manner, the accelerator output electron beam energy level may be adjusted through a simple decision process, and only three conditions are required for the output electron beam energy level of the accelerator to meet its demands, so that device requirements may be reduced, which is adverse to popularization and application.

In an embodiment, the accelerator has multiple output electron beam energy levels, such as P1, P2, . . . Pn (n>3) from low to high, when the object to be inspected is detected with Px, if the detection data is above an upper threshold value Th, the output electron beam energy level is adjusted to Px−1; if the detection data is below a lower threshold value T1, the output electron beam energy level is adjusted to Px+1. In this manner, through setting multiple levels, the output electron beam energy level may be controlled more accurately and conveniently, and an optimal effect of controlling imaging technical indexes and reducing the environmental dose level may be achieved.

Figure 10:
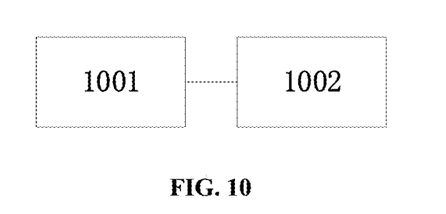
FIG. 10 is a schematic view of an embodiment of the radiation scan controller of this invention.

FIG. 10 shows a schematic view of an embodiment of the radiation scan controller according to this invention. Wherein, a data acquisition module 1001 is capable of acquiring detection data of an object to be inspected under radiation scanning using a detector. An adjustment module 1002 is capable of adjusting working conditions of a radiation emitter according to the detection data acquired by the detector. An accelerator output beam dose rate, or an output electron beam energy level, or both of them may be adjusted.

This controller may adjust working conditions of the accelerator of the radiation emission device according to the detection data detected by the detector, so that for a region having a larger mass thickness, a higher output beam dose rate or a higher electron beam output energy level is adopted to guarantee satisfied imaging technical indexes, for a region having a smaller mass thickness, a lower output beam dose rate or a lower electron beam output energy level is adopted to reduce the environmental dose level while guaranteeing satisfied imaging technical indexes.

In an embodiment, the detection data may be a sampling value of the detector, working conditions of the radiation emitter are adjusted according to the sampling value; or the detection data may be transparency information of the object to be inspected obtained by the detector, and working conditions of the radiation emitter are adjusted according to the transparency information. This controller may adjust working conditions of the radiation emitter according to a sampling value obtained by the detector or transparency information of a detection image. This data may be obtained conveniently and may be processed conveniently, so that system response speed may be improved.

In an embodiment, the adjustment module may obtain detection data in real time as the object to be inspected moves relative to the detector, and adjust working conditions for the accelerator of the radiation emission device in real time. In another embodiment, a sampling value is used as the real-time detection data, if the detector detects an increased sampling value, it indicates that the object to be inspected entering the detection range has a smaller mass thickness, thus the adjustment module decrease the output beam dose rate or the electron beam output energy level; if the sampling value becomes larger, it indicates that the object to be inspected entering the detection range has a larger mass thickness, the adjustment module increases the output beam dose rate or the electron beam output energy level. In another embodiment, transparency information of the object to be inspected is used as the real-time detection data, in the case of increased transparency information, it indicates that the object to be inspected entering the detection range has a smaller mass thickness, the adjustment module decreases the output beam dose rate or the electron beam output energy level; in the case of decreased transparency information, it indicates that the object to be inspected entering the detection range has a larger mass thickness, the adjustment module increases the output beam dose rate or the electron beam output energy level.

This controller may adjust the accelerator output beam dose rate and/or electron beam output energy level in real time during the scanning process, so that detection may be completed in one operation while guaranteeing satisfied imaging technical indexes and reducing environmental dose level, so that detection efficiency is improved.

In an embodiment, after a complete scanning, the adjustment module analyzes all scan data to determine a main scanning region of the object to be inspected, and then detection is performed again for the main scanning region. The particular accelerator output beam dose rate/electron beam output energy level adjusted by the controller may be determined according to the obtained scan data.

This controller may obtain a main scanning region from the scan data, and only the main scanning region is detected using a higher accelerator output beam dose rate and/or a higher electron beam output energy level to realize satisfied imaging technical indexes and a reduced environmental dose level. Compared with real-time detection and adjustment, there is a lower requirement of system response speed and it is more accurate. It also allows the object to be inspected to pass through the detection region at a faster speed.

Figure 11:
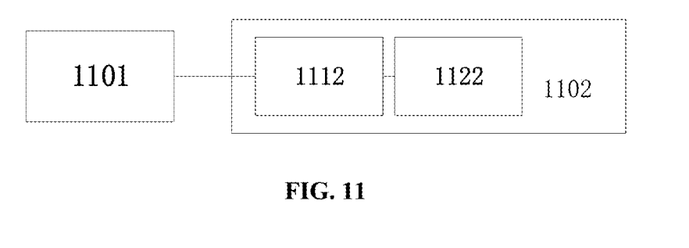
FIG. 11 is a schematic view of another embodiment of the radiation scan controller of this invention.

In an embodiment, as shown in FIG. 11, a data acquisition module 1001 is capable of acquiring detection data of an object to be inspected under radiation scanning using a detector. An adjustment module 1102 comprises a comparison unit 1112 and an emission adjustment unit 1122. If the detection data is a sampling value, the comparison unit 1112 compares the sampling value with a predetermined sampling threshold value. If the sampling value is above the predetermined upper sampling threshold value, the emission adjustment unit 1122 decreases the accelerator output beam dose rate and/or the output electron beam energy level; if the sampling value is below the predetermined lower sampling threshold value, the emission adjustment unit 1122 increases the accelerator output beam dose rate and/or the output electron beam energy level.

This controller may compare the obtained sampling value with the predetermined threshold value to determine whether it is necessary to adjust the accelerator output beam dose rate/electron beam energy level and how to adjust the accelerator output beam dose rate/electron beam energy level, which has advantages of clear in logic, concise calculation, low requirements of the processing device, and easy to be popularized and applied. Meanwhile, adjustment is required only if a certain threshold value has been reached, so that the number of times the adjustment is performed may be reduced, and the device load may be decreased.

In an embodiment, if the detection data is transparency information, the comparison unit 1112 compares the transparency information with a predetermined transparency threshold value. If the transparency information is above a predetermined upper transparency threshold value, the emission adjustment unit 1122 decreases the accelerator output beam dose rate and/or the output electron beam energy level; if the transparency information is below a predetermined lower transparency threshold value, the emission adjustment unit 1122 increases the accelerator output beam dose rate and/or the output electron beam energy level.

This controller may compare the obtained transparency information with a predetermined threshold value to determine whether it is necessary to adjust the accelerator output beam dose rate/electron beam energy level and how to adjust the accelerator output beam dose rate/electron beam energy level, which has advantages of clear in logic, concise calculation, low requirements of the processing device, and easy to be popularized and applied. Meanwhile, adjustment is required only if a certain threshold value has been reached, so that the number of times the adjustment is performed may be reduced, and the device load may be decreased.

In an embodiment, an ideal value determination unit 1112 in FIG. 11 is capable of determining an ideal accelerator working condition based on the detection data according to a predetermined policy; based on the obtained detection data, according to a predetermined conversion policy, such as a linear relationship or a conversion formula, an ideal accelerator output beam dose rate or an ideal electron beam output energy level may be determined. An emission adjustment unit 1122 adjusts working conditions of a radiation emitter according to the ideal values. This controller may adjust working conditions of the radiation emitter with a smaller granularity and more accurately, so that detection accuracy may be further improved.

Figure 12:
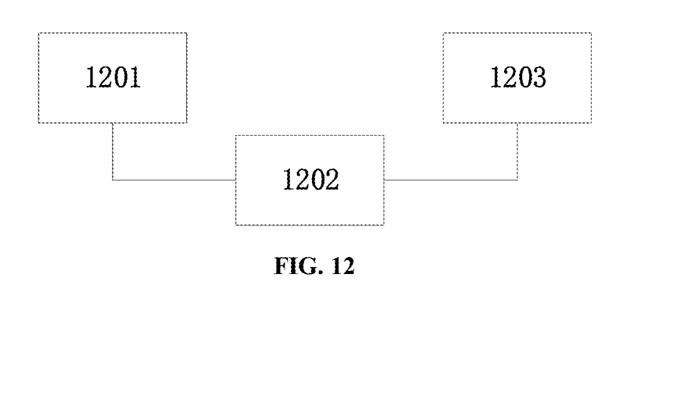
FIG. 12 is a schematic view of an embodiment of a scan system of this invention.

FIG. 12 shows a schematic view of an embodiment of the scan system according to this invention. Wherein, the detector 1201 is capable of obtaining detection data and sending to a controller. The controller 1202 is capable of determining whether it is necessary to adjust the accelerator output beam dose rate/electron beam energy level and how to adjust the accelerator output beam dose rate/electron beam energy level, generating control information and sending to the radiation emitter. The radiation emitter 1203 is capable of radiating on object to be inspected and adjusting working conditions of an accelerator according to the control information obtained from the controller 1202.

This scan system may adjust working conditions of the accelerator of the radiation emission device according to the detection data detected by the detector, so that for a region having a larger mass thickness, a higher output beam dose rate or a higher electron beam output energy level is adopted to guarantee satisfied imaging technical indexes, for a region having a smaller mass thickness, a lower output beam dose rate or a lower electron beam output energy level is adopted to reduce the environmental dose level while guaranteeing satisfied imaging technical indexes.

Figure 13:
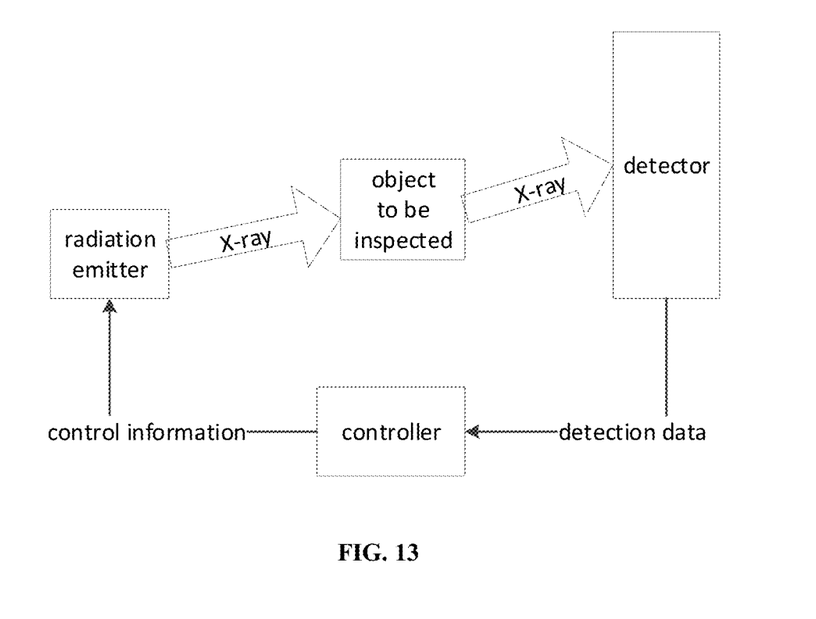
FIG. 13 is a schematic view of another embodiment of the scan system of this invention.

In an embodiment, as shown in FIG. 13, a radiation emitter emits X-ray to an object to be inspected, the X-ray penetrates the object to be inspected and reaches a detector. The detector acquires detection data and forwards to a controller. The controller determines whether to and how to adjust working conditions of the radiation emitter based on the detection data. If it is required to adjust working conditions of the radiation emitter, control information is generated and sent to the radiation emitter for adjustment, to control the accelerator of the radiation emitter to increase or decrease its output beam dose rate/output electron beam energy level.

Through coordination between the radiation emitter, the detector and the controller, working conditions of the radiation emitter are adjusted according to the mass thickness of the object to be inspected and particular situations, so that satisfied imaging technical indexes may be guaranteed while reducing the environmental dose level.

It shall be noted that: the above embodiments are merely illustration of the technical solution of this invention, but are not limitation thereof. Although this invention has been described in detail with preferred embodiments, those ordinary skilled in the art shall understand: embodiments of the present invention may be modified or some technical features thereof may be substituted equivalently, without departing from the spirit of the technical solution of this invention, all of which shall be encompassed in the scope of the technical solution as claimed in this invention.

What is claimed is:

1. A scanning method, comprising:
acquiring initial transparency information according to detection data of an object to be inspected acquired under radiation scanning by a detector;
correcting the initial transparency information according to a background image and an air image to obtain the transparency information; and
adjusting an accelerator output beam dose rate and/or an output electron beam energy level of a radiation emission device according to the detection data.

2. The method according to claim 1, wherein adjusting an accelerator output beam dose rate and/or an output electron beam energy level of a radiation emission device according to the detection data comprises:
during a movement of the object to be inspected relative to the radiation emission device and the detector, adjusting an accelerator output beam dose rate and/or an output electron beam energy level of a radiation emission device according to real-time detection data obtained by the detector from a scanning region of the object to be inspected.

3. The method according to claim 1, wherein adjusting an accelerator output beam dose rate and/or an output electron beam energy level of a radiation emission device according to the detection data comprises:
acquiring overall scanning data of the object to be inspected using the detector;
analyzing the overall scanning data to determine a main scanning region of the object to be inspected, wherein the main scanning region comprises a low penetration region or a region suspected to be a contraband item;
determine an accelerator output beam dose rate and/or output electron beam energy level according to detection data of the main scanning region, to scan the main scanning region.

4. The method according to claim 1, wherein the detection data is transparency information of the object to be inspected;
adjusting an accelerator output beam dose rate and/or an output electron beam energy level of a radiation emission device according to the detection data comprises:
comparing the transparency information with a predetermined transparency threshold value;
if the transparency information is below a predetermined lower transparency threshold value, increasing the accelerator output beam dose rate and/or the output electron beam energy level; and
if the transparency information is above a predetermined upper transparency threshold value, decreasing the accelerator output beam dose rate and/or the output electron beam energy level.

5. The method according to claim 1, wherein adjusting an accelerator output beam dose rate and/or an output electron beam energy level of a radiation emission device according to the detection data comprises:
determining an ideal output beam dose rate and/or an ideal output electron beam energy level according to a conversion policy for converting the detection data to the ideal accelerator output beam dose rate and/or the ideal output electron beam energy level; and
adjusting the accelerator output beam dose rate and/or the output electron beam energy level to the ideal output beam dose rate and/or the ideal output electron beam energy level.

6. The method according to claim 1, wherein the accelerator of the radiation emission device comprises multiple output beam dose rate levels and/or multiple output electron beam energy levels, each level having a fixed output beam dose rate and/or a fixed output electron beam energy value;
adjusting an accelerator output beam dose rate and/or an output electron beam energy level of a radiation emission device according to the detection data comprises:
adjusting the accelerator output beam dose rate and/or the output electron beam energy level of the radiation emission device to a certain level according to the detection data.

7. A radiation scan controller, characterized in comprising:
a data acquisition module for acquiring initial transparency information according to detection data of an object to be inspected acquired under radiation scanning by a detector; correcting the initial transparency information according to a background image and an air image to obtain the transparency information; and
an adjustment module for adjusting an accelerator output beam dose rate and/or an output electron beam energy level of a radiation emission device according to the detection data.

8. The controller according to claim 7, wherein the adjustment module is further used for:
during a movement of the object to be inspected relative to the radiation emission device and the detector, adjusting an accelerator output beam dose rate and/or an output electron beam energy level of a radiation emission device according to real-time detection data obtained by the detector from a scanning region of the object to be inspected.

9. The controller according to claim 7, wherein the adjustment module is further used for:
acquire overall scanning data of the object to be inspected;

analyzing the overall scanning data to determine a main scanning region of the object to be inspected, wherein the main scanning region comprises a low penetration region or a region suspected to be a contraband item; and determine an accelerator output beam dose rate and/or an output electron beam energy level according to detection data of the main scanning region, to scan the main scanning region.

10. The controller according to claim 7, wherein the detection data is transparency information of the object to be inspected;

the adjustment module further comprises:
a comparison unit for comparing the transparency information with a predetermined transparency threshold value; and
an emission adjustment unit for, if the transparency information is below a predetermined lower transparency threshold value, increasing the accelerator output beam dose rate and/or the output electron beam energy level; if the transparency information is above a predetermined upper transparency threshold value, decreasing the accelerator output beam dose rate and/or the output electron beam energy level.

11. The controller according to claim 7, wherein the adjustment module further comprises:
an ideal value determination unit for determining an ideal output beam dose rate and/or an ideal output electron beam energy level according to a conversion policy for converting the detection data to the ideal accelerator output beam dose rate and/or the ideal output electron beam energy level; and
an emission adjustment unit for adjusting the accelerator output beam dose rate and/or the output electron beam energy level to the ideal output beam dose rate and/or the ideal output electron beam energy level.

12. The controller according to claim 7, wherein the accelerator of the radiation emission device comprises multiple output beam dose rate levels and/or multiple output electron beam energy levels, each level having a fixed output beam dose rate and/or a fixed output electron beam energy value; and the adjustment module is further used to adjust the accelerator output beam dose rate and/or the output electron beam energy level of the radiation emission device to a certain level according to the detection data.

13. A scanning system, comprising:
a controller of claim 7;
a detector; and
a radiation emitter;
wherein the detector is used to send detection data to the controller;
the controller is used to send control information to the radiation emitter for adjusting an accelerator output beam dose rate and/or an output electron beam energy level of the radiation emission device according to the detection data; and
the radiation emitter is used for emitting radiation; adjusting an accelerator output beam dose rate and/or an output electron beam energy level of a radiation emission device according to the detection data.

* * * * *